United States Patent
Leonardo et al.

(10) Patent No.: US 11,742,066 B1
(45) Date of Patent: Aug. 29, 2023

(54) SYSTEM AND METHOD FOR PATIENT PRESCRIPTION VERIFICATION

(71) Applicant: WALGREEN CO., Deerfield, IL (US)

(72) Inventors: Nicolet L. Leonardo, Palatine, IL (US); Averill D. Gordon, Grayslake, IL (US); Ugochi C. Baker, Chicago, IL (US)

(73) Assignee: WALGREEN CO., Deerfield, IL (US)

( * ) Notice: Subject to any disclaimer, the term of this patent is extended or adjusted under 35 U.S.C. 154(b) by 372 days.

(21) Appl. No.: 16/686,790

(22) Filed: Nov. 18, 2019

Related U.S. Application Data

(63) Continuation of application No. 14/848,660, filed on Sep. 9, 2015, now Pat. No. 10,503,874.

(60) Provisional application No. 62/065,466, filed on Oct. 17, 2014.

(51) Int. Cl.
   *G16H 20/10* (2018.01)

(52) U.S. Cl.
   CPC ................... *G16H 20/10* (2018.01)

(58) Field of Classification Search
   CPC ........................................... G16H 20/10
   USPC ............................................. 705/2-4
   See application file for complete search history.

(56) References Cited

U.S. PATENT DOCUMENTS

| | | | | |
|---|---|---|---|---|
| 8,639,523 | B1* | 1/2014 | Pinsonneault | G16H 20/10 705/2 |
| 8,914,298 | B1 | 12/2014 | Luciano | |
| 2002/0032582 | A1* | 3/2002 | Feeney, Jr. et al. | G16H 20/13 705/2 |
| 2005/0240441 | A1* | 10/2005 | Suzuki et al. | G16H 40/20 705/2 |
| 2007/0168221 | A1 | 7/2007 | Blotter et al. | |
| 2008/0306761 | A1* | 12/2008 | George et al. | G06Q 10/10 705/2 |
| 2013/0325496 | A1* | 12/2013 | Nasso | G16H 20/10 705/2 |

OTHER PUBLICATIONS

Final Office Action for U.S. Appl. No. 14/848,660 dated Feb. 13, 2019.
Non-Final Office Action for U.S. Appl. No. 14/848,660 dated Oct. 12, 2018.
Notice of Allowance for U.S. Appl. No. 14/848,660 dated Aug. 7, 2019.
Schneider, Philip J., "Pharmacists Building a Safer Health System", American Journal of Health-System Pharmacy 58.1 (2001), pgs. 66-68.

* cited by examiner

*Primary Examiner* — Mark Holcomb
(74) *Attorney, Agent, or Firm* — Marshall, Gerstein & Borun LLP; Randall G. Rueth

(57) ABSTRACT

A system to verify the identity of a recipient requesting fulfillment of a prescription for a pharmaceutical product includes a point-of-sale retail personal identification number entry device (pinpad) and a workstation that stop a transaction for the pharmaceutical product from proceeding in response to a request associated with a claim for dispensing the pharmaceutical product. A first input for data identifying a member of a rewards program is entered with the pinpad, and a second input for data identifying a recipient of the prescription is entered with the workstation. The workstation compares the data identifying the member of the rewards program against the data identifying the recipient of the prescription. If there is a match between the data identifying the member of the rewards program and the data identifying the recipient of the prescription, the pinpad and workstation allow the transaction for the pharmaceutical product to proceed.

20 Claims, 10 Drawing Sheets

Patient Verification

Patients Name:

Olga

Please enter the last four digits
  of the patient's Phone Number (555) 555 – ▢

[ ENTER ]   [ DON'T KNOW ]

*FIG. 10*

SYSTEM AND METHOD FOR PATIENT PRESCRIPTION VERIFICATION

RELATED APPLICATIONS

This application is a continuation of U.S. Pat. Application No. 14/848,660 entitled "SYSTEM AND METHOD FOR PATIENT PRESCRIPTION VERIFICATION", filed Sep. 9, 2015 which claims priority, under 35 U.S.C. § 119, to U.S. Provisional Pat. Application No. 62/065,466, filed on Oct. 17, 2014, entitled "SYSTEM AND METHOD FOR PATIENT PRESCRIPTION VERIFICATION," the entirety of which are hereby incorporated herein by reference for all purposes.

FIELD OF THE INVENTION

The present invention relates to a method and system for verifying the identity of a patient picking up a prescription and to verify that the patient is receiving the correct prescription. An embodiment of the method and system includes hardware, software, and pharmacy workflows for verifying the patient's identity and the correct prescription.

BACKGROUND

The interaction between a pharmacist and a patient is often at its most important when a patient is picking up a prescription. In particular, great care needs to be taken so that the patient receives the correct prescription. Receiving the wrong prescription has the potential for significant adverse health outcomes either because of the patient has an adverse effect in response to receiving the wrong prescription or has an adverse health effect in response to not having the correct prescription. Likewise, another patient may receive the prescription intended for the first patient, and also have an adverse health effect as a result. As such, there exists a strong safety issue in ensuring that patients receive the correct prescription.

Generally, the only insurance that a patient receives the correct prescription is the pharmacist, or personnel authorized by the pharmacist, completing the transaction for the prescription. Typically, the pharmacist manually asks the patient to verify his/her address or other form of identifying information, and compares the response provided by the patient with information presented on a workstation in connection with a datafile on the patient's prescription. If the information corresponds to what the pharmacist sees, the pharmacist proceeds with the transaction for the prescription. Reliance upon a pharmacist to ask the patient for identifying information necessarily introduces variance into the procedure, in that the pharmacist may not always be consistent in asking the same information from the patient to verify the prescription.

BRIEF DESCRIPTION OF THE DRAWINGS

FIG. 10 is a screen shot of a patient profile look-up PIN entry device interface page.

DETAILED DESCRIPTION

For purposes of the present disclosure, a pharmacy may be any of the outlets through which an entity implementing the present patient verification system sells prescription medications to patients. For example, the pharmacy may comprise a single independent drug store or any one of a number of branch stores in a large drugstore chain. The pharmacy may also be or include a mail-order or on-line pharmacy, and one or more specialty pharmacies dealing in rare expensive medications or drugs that require special administering procedures. Typically, the pharmacy will have a direct relationship with a very large number of patients. Because of the direct relationship between the pharmacy and such a vast pool of individual patients, the pharmacy is ideally placed to provide a number of medication therapy management services of significant value to both the patients and various stakeholders in the medical services delivery community.

Figure 1:
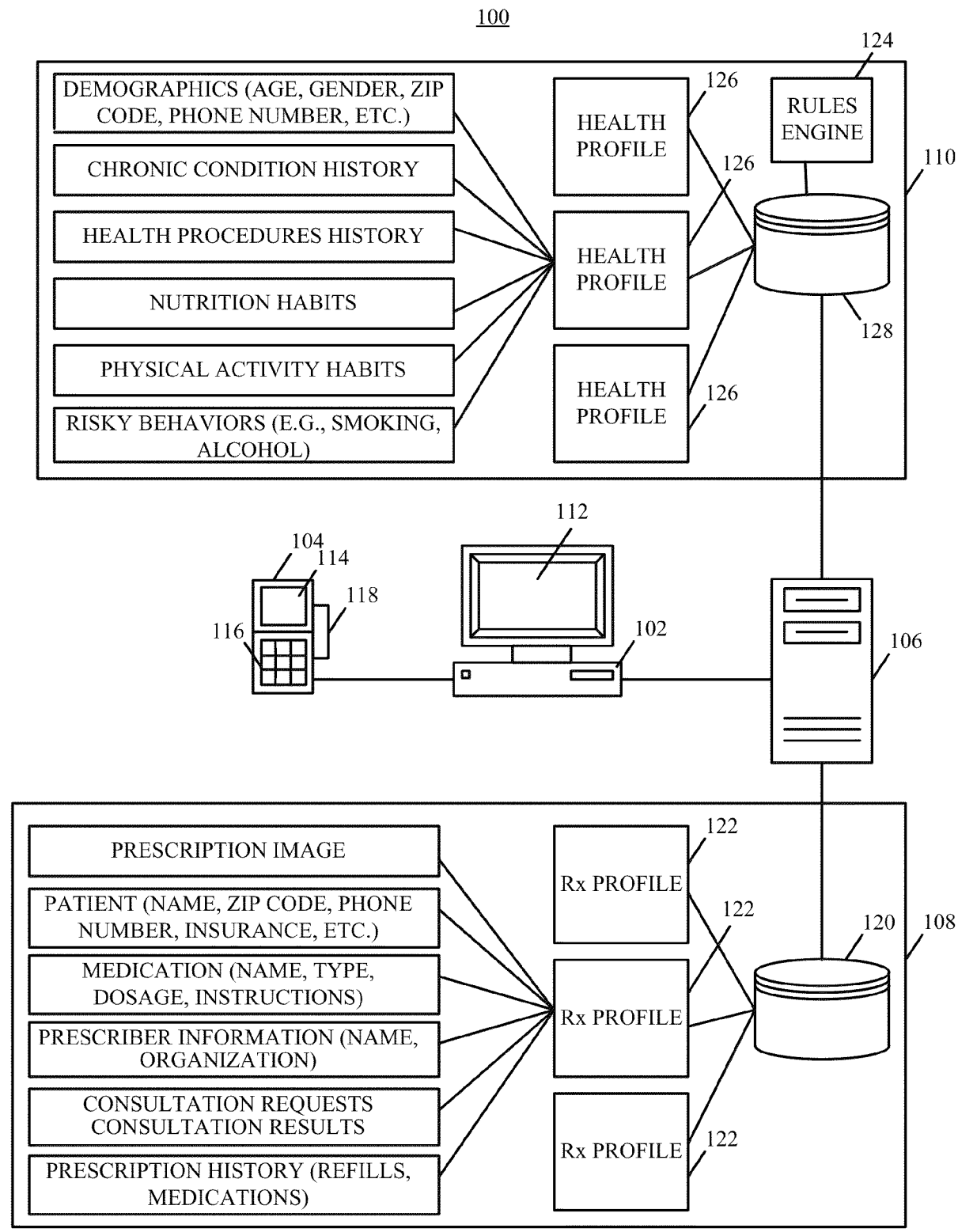
FIG. 1 is a block diagram of an exemplary patient verification system for verifying the identity of a patient picking up a prescription.

FIG. 1 shows a block diagram of the architecture of an embodiment of a patient verification system 100. The systems and processes implemented by the patient verification system 100 facilitate the verification of a prescription for a patient at a pharmacy, and, more particularly, at a point-of-sale (POS) within the pharmacy, such as at a pharmacy workstation at a pharmaceutical pick-up counter or cash register. Nonetheless, the patient verification system 100 may be implemented on a scale that allows any number of individual patients to be verified by the patient verification system 100. The high-level architecture includes both hardware and software applications, as well as various data communications channels for communicating data between the various hardware and software components. The patient verification system 100 may be divided into front-end components 102, 104, 106 and backend components 108, 110. The front-end components comprise the hardware and software components associated with a pharmacy's sales outlets. For example, a pharmacy may include a number of retail branch stores, an on-line pharmacy, a mail order pharmacy and a specialty pharmacy. The front end components may comprise the hardware and software applications found in each of the pharmacy's retail outlets. For the purposes of this application, the point-of-sale refers to the point-of-sale at a retail branch store or other in-person interaction between the patient and a pharmacist, pharmaceutical technician or other person authorized to distribute pharmaceutical products or complete a transaction for a pharmaceutical product.

The retail branch stores may include one or more pharmacy workstations 102, point-of-sale retail Personal Identification Number (PIN) entry devices 104 and application servers 106. The pharmacy workstations 102 may include software applications for managing pharmacy operations, including filling patient prescriptions, and the like. The pharmacy workstations 102 may also include software applications for implementing the present patient verification systems. The pharmacy workstations 102 may also function as point-of-sale (POS) terminals for performing cash register functions and certain patient verification functions associated with the patient verification system 100, as will be described. The pharmacy workstation 102 may include an LCD 112 or other display device for displaying messages to the pharmacist or other pharmacy personnel. (For the remainder of the present disclosure all pharmacy personnel will be referred to as "the pharmacist" even though various tasks within the pharmacy may be performed by personnel who are not registered pharmacists but who operate under a pharmacist's supervision.) The pharmacy workstation 102 may also include a bar code reader for reading bar codes on prescriptions and product packaging and the like. The individual pharmacy workstations 102 at a particular store may be connected to an in-store local area network. The local area network couples the pharmacy workstation 102 to the application server 106 which communicates with the backend systems 108, 110 over a wide area network. A similar arrangement may be found in the pharmacy's other divisions such as an on-line pharmacy, a mail order pharmacy, a specialty pharmacy, or the like. The wide area network may be a proprietary network, a secure public internet, a virtual private network or some other type of secure network.

The local area network may also couple the pharmacy workstation 102 to the PIN entry device 104. Generally speaking, the PIN entry device 104, such as a PIN pad terminal, is understood to be an electronic device used in electronic- and/or cash-based transactions to accept and encrypt a person's PIN as associated with a debit, credit or smart card so that the card may be accessed for payment. As will be discussed further herein, the PIN entry device 104 may also be used to read information from a rewards card or other membership indicia associated with a health and wellness rewards program of which the patient is a member (e.g., enrolls in and/or has a health and wellness rewards program account). The PIN entry device 104 may include an LCD 114 or other display device for displaying messages to the patient or other customer. (For the remainder of the present disclosure all persons picking up a prescription will be referred to as "the patient" even though various tasks in picking up the prescription may be performed by persons authorized to pick up the prescription on behalf of the actual patient.) The PIN entry device 104 may also include an alphanumeric keypad 116 to allow the patient to make selections to verify his/her identity and complete the transaction. A membership identification reader 118, such as a magnetic card reader, radio frequency identification (RFID) reader, bar code reader, or the like, for reading the patient's card(s) may be included. Alternatively or in addition, the PIN entry device 104 may include a short-range wireless transceiver (e.g., Bluetooth, RFID, near field communication, etc.) that can communicate with a patient's mobile device (e.g., smartphone, tablet, etc.) that is similarly enabled for short-range wireless communication in order to read account information for payment, rewards, etc., where the mobile device is used as a mobile payment system (e.g., a "digital wallet"), as is understood by those skilled in the relevant art(s).

The backend components include central processing systems and legacy systems and services 108. The legacy systems and services 108 may include a pharmacy's existing hardware and software systems associated with the delivery of pharmacy services to patients. For example, the legacy systems 108 may execute software applications supporting pharmacy operations, including filling patient prescriptions, keeping track of patients' fill histories, and the like. The legacy systems 108 may also provide ad hoc medication management services that may be integrated into the patient verification system 100. The legacy systems 108 may include legacy data stores 120 for storing patient information such as the patient's name, address, phone number, insurance carrier, prescription history, and the like, for all patients who have purchased prescription medications from the pharmacy. An example of a legacy system and services 108 includes Walgreen's Intercom Plus system, and examples of patient information that may be stored by the legacy systems 108 includes patient prescription profiles 122.

Generally speaking, a patient prescription profile 122 is an aggregation of several aspects of a patient. The patient prescription profile 122 depicted in FIG. 1 is an exemplary embodiment of data that is utilized by the pharmacy to maintain and track health information about the patient. In the exemplary embodiment shown in FIG. 1, the patient prescription profile 122 includes data representing patient personal information (e.g., name, address, phone number, insurance provider/plan, government health programs, etc.), current and past medications (e.g., medication name, medication type, dosages, instructions, etc.), prescriber information (e.g., prescribing doctor, prescribing organization, doctor's employer), consultations (e.g., consultation history, consultation requests, consultation results, eligible consultations, etc.) and/or prescription history (e.g., refills, medications, dosage, instructions, etc.). The patient prescription profile 122 may also include information on other patients, such as dependents, within the patient's household for whom the patient is otherwise authorized to pick up prescriptions. Aspects of these additional patients, similar to the patient aspects mentioned above, may be maintained as part of the patient prescription profile 122 or may be maintained as separate patient prescription profiles, whereby patient prescription profiles of patients within the same household are logically linked to one another so that any of the patients within the same household may pick up a prescription for themselves and others within the household.

The aspects of patient prescription profile 122 can be obtained by the legacy systems and services 108 through several means. Typically, as part of the onboarding procedure for a new patient, a pharmacy acquires some of these aspects. Additional aspects of the patient prescription profile 122 can be obtained via other means, such as a questionnaire sent to the patient, medical records, medical history obtained from an insurance provider, partner pharmacies, including partner retail branch stores, on-line pharmacy, mail order pharmacy and specialty pharmacy, etc.

An additional backend component may include a loyalty system 110 as part of a loyalty program. As is understood by those of ordinary skill in the relevant art(s), a loyalty program is a structured marketing effort that rewards or otherwise encourages certain behavior from its members. For example, a loyalty program may be retailer- and/or employer-based that rewards consumer/employee activities beneficial to the retailer or employer. In one example, consumers may be awarded rewards points as virtual currency or discounts for buying goods and services from a particular retailer, which may then be applied to the purchase of further goods and services, and a retailer can track which goods and services are purchased by each member. In another example, employees may be awarded rewards points for work performance, attendance, good work habits, good health habits, etc. from an employer, which may then be applied to receive additional vacation days, gift cards or other items of financial or personal value. As disclosed herein, an embodiment of the loyalty system 110 is a health and wellness rewards system as part of a retailer- and/or employer-based health and wellness rewards program, though any of a number of different loyalty programs may be utilized without significant departure from the disclosed system 110 and without departure from the scope of this disclosure.

The health and wellness rewards system 110 may include a pharmacy's hardware and software systems associated with the accumulation, retention and utilization of rewards points for patients. For example, the health and wellness rewards system 110 may execute one or more rules engines 124 supporting various modules that represent different functioning components of the overall health and wellness rewards system. A rules engine 124 is an aggregation of various modules that perform corresponding functionalities within the health and wellness rewards system. The rules engine 124 may be a consolidated engine that is located at a single location, such as a server, for example. Each of the corresponding modules operates on data that is received from another source in accordance with its respective functionality. In other examples, the rules engine 124 is a collection of various modules that are located at more than one location, and, in accordance, the rules engine 124 offloads the respective processing at each module in accordance with its respective functionality.

Generally, the rules engine 124 is implemented by the retailer pharmacy and is configured to receive and/or monitor data from one or more sources, and to process data from one or more sources to generate outcomes data. The outcomes data indicates which reward incentives were effective for modifying behaviors of one or more patients. In the aggregate, therefore, the outcomes data represents a measure of effectiveness of various incentives for a population sample that includes the participating patient members in the health and wellness plan. (For the remainder of the present disclosure all patients that participate in, or have an account or membership with, the health and wellness rewards program will be referred to as a "patient member".) Once aggregated over time and with larger population samples, the outcomes data can provide key insights regarding how to influence the behavior of their present and subsequent members with better efficiency.

The rules engine 124 may receive data from one or more sources such as retail data, web usage data, intervention history, health profile data, and prescription data. As shown in FIG. 1, the health profile data is an implementation of a health profile 126. The retailer pharmacy provides the reward points as virtual currency to purchase its goods and services, and can track which goods and services are purchased by each patient member when the points are redeemed. Because a patient member needs to log in to either a POS or online to redeem the accrued reward points, the retailer pharmacy can track this information and store it appropriately as it is gathered. Retail and web usage data may also be acquired for one or more patient members even when a patient member is not redeeming reward points. For example, the retailer pharmacy may use a loyalty program that provides discounts when purchased with the loyalty card at a POS. Furthermore, many retailers also require or encourage customers to log in to their website when purchasing their goods and services. Data acquired via these methods is also collected by the rules engine 124.

The rules engine 124 may include several modules that each may represent the functionality and/or processing implemented within each respective system. In this way, the rules engine 124 represents an amalgamation of several infrastructures. For example, the rules engine 124 is an amalgamation of infrastructures and/or data that are available to the retailer pharmacy. As a result, the rules engine 124 may be implemented in an embodiment as one or more algorithms that use this infrastructure and do not require additional hardware and/or additional interfaces, thereby simplifying the implementation of the rules engine 124. Examples of modules constituting the rules engine 124 include a balance rewards framework, a personalization engine, an analytics engine, a loyalty platform, a campaign manager, and a reporting engine. A balance rewards framework module includes the appropriate servers and infrastructure that determine which activities are rewarded, and the appropriate initial rewards for each qualifying activity.

A personalization engine module determines an initial and/or subsequent rules strategy for allocating reward points based on each patient member's health profile. A health profile 126 may include, for example, health profile data and/or any other relevant data which may be used to formulate a reward point strategy. The health profile 126 could be complied with information obtained, for example, from any suitable data that is received by the rules engine 124, such as retail data, web usage data, intervention history, health profile data, and prescription data. The personalization engine may further modify the allocation of reward points for corresponding behaviors based on each particular member profile. Alternatively or in addition, the personalization engine may modify the allocation of reward points to target a specific desired behavior corresponding to one or more characteristics that are common among one or more patient members. For example, the personalization engine could modify the reward points for one or more specific behaviors for all patient members who have diabetes. In various embodiments, the personalization engine sets reward points rules based on one or more suitable factors, which could include feedback received from subsequent patient member behaviors in response to granted reward points, or other data as it is received and/or updated from other modules constituting the rules engine 124. Once the personalization engine sets the rules and/or strategies for one or more patient members, this information is shared with one or more other modules constituting the rules engine 124, such as the balance rewards framework module, for example, so the appropriate behaviors and their corresponding reward point values are updated for each patient member.

The analytics engine may be configured to collect and/or aggregate various sets of data relevant to the health and wellness program. This data could include, for example, online marketing data, web analytics data, etc., and could be grouped by one or more geographic member regions. This data may be related to spending habits of one or more patient members, which could be online or in-store. The in-store and online spending data could correspond to other websites and/or retailers in addition to the rewards partner retailer. For example, this data could be purchased or mined from a source that is separate or integrated as part of the partner retailer's own analytical systems. In various embodiments, the analytics engine shares this received and/or processed data with one or more of the modules constituting the rules engine 124. In this way, the personalization rules engine module may adapt and update reward point rules and/or strategies based on newly acquired analytics engine data.

The loyalty platform module may be configured to collect and/or aggregate data from one or more loyalty marketing sources. This data could represent, for example, loyalty marketing services, database marketing, direct mail, email marketing, web development, etc. Examples of loyalty marketing data could include additional demographic information on patient members that is relevant to the health and wellness rewards allocation, such as marital status, number of children, income, etc. In various embodiments, the analytics engine shares this received and/or processed data with one or more of the modules constituting the rules engine 124. In this way, the personalization rules engine module may adapt and update reward point rules and/or strategies based on newly acquired loyalty platform data.

The campaign manager module may be configured to generate targeted campaigns for one or more patient members based on member data. These campaigns could be generated, for example, for various groups of patient members based on each group's geographic location, age, income level, history of commonly-engaged behaviors, etc. In this way, the campaign manager module generates one or more separate sets of balance rewards campaigns for one or more patient members and/or patient member groups. The campaign manager module shares the generated campaigns and/or processed data with one or more of the modules constituting the rules engine 124, and the personalization rules engine module may adapt and update reward point rules and/or strategies based on newly acquired loyalty platform data.

The reporting engine module may be configured to analyze the data gathered from one or more of the other modules constituting the rules engine 124 and/or data received by the rules engine 124 (such as retail data, etc.) and generate one or more reports as outcomes data. The outcomes data represents the behavior of one or more patient members (or groups of patient members) based on the reward points provided for specific member activities (i.e., interventions). The outcomes data includes a history of various rewards points for each patient member for which reward points incentives worked versus those that did not work. In other words, the outcomes data indicates the incentives granted (i.e., a number of reward points) to one or more members in exchange for the one or more patient members completing their corresponding interventions. In this way, the outcomes data includes the subsequent results of patient member behavior in response to one or more reward point incentives.

For example, if a patient member's health profile indicates that a diabetic member is already an avid walker, the personalization engine module could adjust the reward point allocations to grant that particular member less reward points for walking (since the incentive is not needed), but more points for blood glucose monitoring. The outcomes data includes a report of whether this adjustment process worked for this patient member by providing a history of subsequent glucose monitoring interventions once the personalization engine had made this reward point adjustment. Furthermore, because the outcomes data is generated for each participating patient member (or group of patient members), the outcomes data indicates what types of incentives produced wanted behavioral changes across a population that includes these patient members or groups of patient members. As will be appreciated by those of ordinary skill in the relevant art(s), the outcomes data can be tailored and/or filtered to accommodate any suitable sub-group of participating patient members, such as age, demographics, etc. In this way, the outcomes data provides valuable insight to what is required to change each respective population group's behavior to incorporate healthier lifestyle habits.

The health and wellness rewards system 110 may include data stores 128 for storing the health profiles 126 for the patient members. Generally speaking, a health profile 126 is an aggregation of several aspects of a patient member. As discussed above, reward points associated with a number of activities can be adjusted. For example, the determination of the allocation of reward points is personalized based on each patient member. The health profile 126 is an exemplary embodiment of data that is utilized by the health and wellness rewards system 110 to personalize reward points. In the exemplary embodiment shown in FIG. 1, the health profile 126 includes data representing member demographics (e.g., age, gender, zip code, phone number, etc.), a chronic condition history, a health procedures history, nutrition habits, physical activity habits, and/or risky behaviors (e.g., smoking, alcohol, etc.).

The aspects of health profile 126 can be obtained by health plan provider through several means. Typically, as part of the onboarding procedure for a new patient member, a health plan provider acquires some of these aspects. Additional aspects of health profile 126 can be obtained via other means, such as public records, a questionnaire sent to the patient member, medical records, retail shopping history obtained from the partner retailer, previously submitted physical activities for reward points, retail shopping history purchased from other retailers, etc. Although disclosed as a health profile in connection with a health and wellness rewards program and system, the health profile is essentially a profile or data structure that is maintained and updated for members of the loyalty program. As such, other member profiles in accordance with the corresponding loyalty program may be utilized without significant departure from the disclosed health profile 126 and without departure from the scope of this disclosure.

Figure 2:
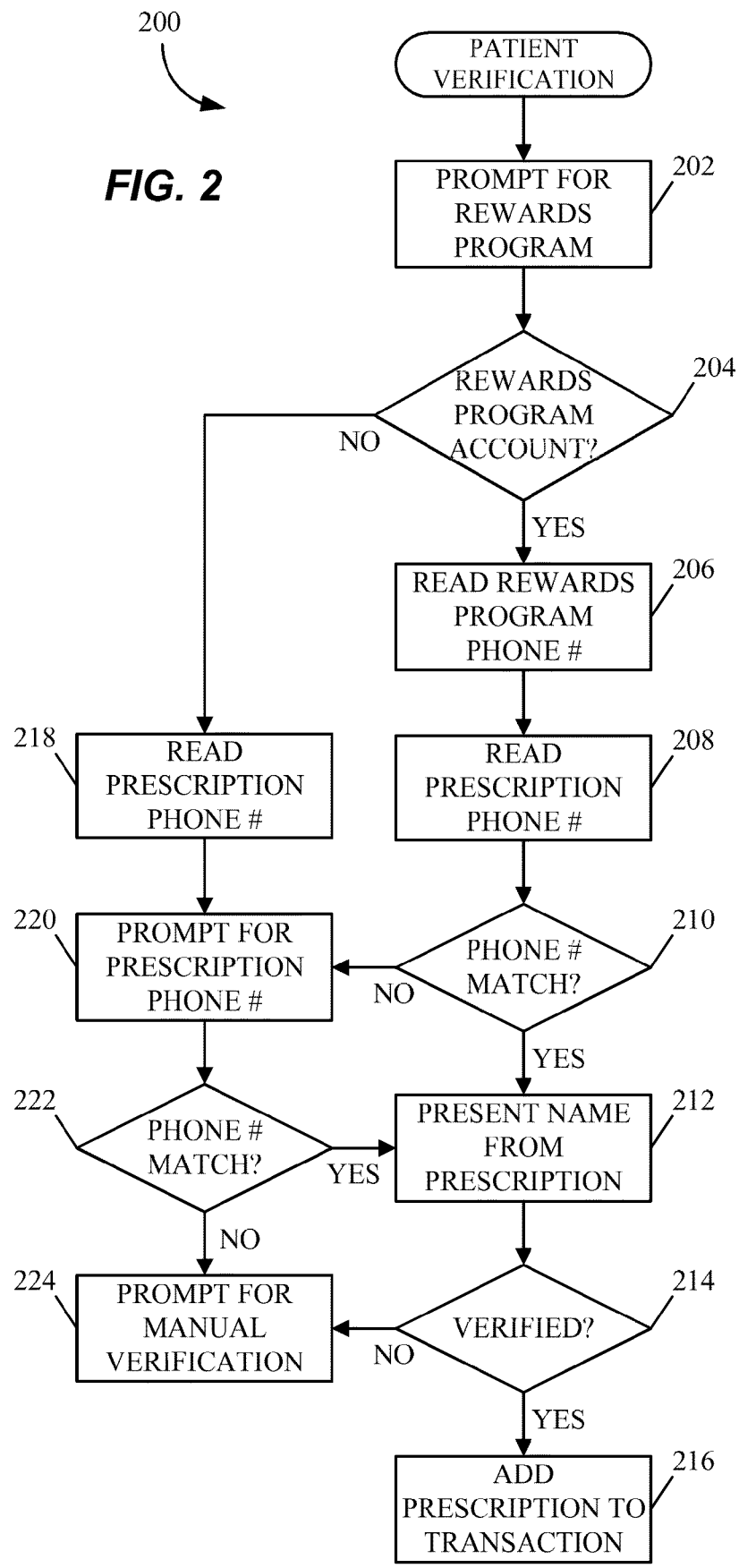
FIG. 2 is a flowchart illustrating an exemplary process for verifying the identity of a patient picking up a prescription.

FIG. 2 illustrates an example of a patient verification routine 200 for verifying the identity of a patient picking up a prescription which may be executed within the patient verification system 100, and, more particularly, by the workstation 102 and the PIN entry device 104. However, it is understood that the patient verification routine 200 may be executed on different computer processors, either as a remote application or as a distributed shared application. For example, the patient verification routine 200 may be executed on the application server 106 such that it may be accessed and utilized by any of the workstations 102 and PIN entry devices 104 throughout the retail pharmacy store via the local area network. Still further, the routine 200 may be executed remotely, for example as part of the legacy system and services 108, and utilized by any of the application servers 106, workstations 102 and/or PIN entry devices 104 throughout a network of pharmacy retail stores via the wide area network. For example, each pharmacy workstation 102 may include a web browser application. The web pages may be served by the application server 106 which acts as a web server, and the pages are displayed by the web browser applications on the pharmacy workstations 102, providing a graphical user interface by which pharmacists may interact with the patient verification system 100. The various web pages forming the user interface may include data pulled from both the legacy stores 128 of the health and wellness rewards system 110 and the legacy data stores 120 of the legacy system and services 108. Furthermore, the workstation 102, PIN entry device 104 and application server 106 may also rely on software applications executed by legacy systems 108 when legacy software applications provide services and other functionality that are incorporated into a comprehensive medication management program.

Generally, the patient verification routine 200 utilizes identifying information from the legacy system and services 108 and the health and wellness rewards system 110 to assist in verifying the patient's identity prior to completing the transaction when the patient picks up a prescription. This enhanced verification helps reduce the chance that a prescription is sold to the wrong patient, helps ensure the safety of patients who might otherwise receive the wrong prescription, and helps improve overall quality. More particularly, the patient verification system 100 and the patient verification routine 200 provide additional verification in addition to manual verification performed by the pharmacist by prompting the patient to enter identifying information (or membership identification information via which identifying information can be retrieved) associated with the patient's health profile 126 in the health and wellness rewards system 110 and/or enter identifying information associated with the patient prescription profile 122 in the legacy system and services 108, and compare the identifying information to that stored in the patient prescription profile 122. If the identifying information matches, the transaction for the prescription is allowed to proceed.

In the embodiment disclosed below, the identifying information is the patient's phone number, and, more particularly, the patient's phone number(s) as associated with the health profile 126 and as associated with the patient prescription profile 122. However, those of ordinary skill in the relevant art(s) will understand that different forms of identifying information may be used instead of the patient's phone number(s), such as, for example, the patient's address, a personal identification number, a password, etc.

FIGS. 3-10 are screenshots of graphical user interfaces presented on the display 112 of the workstation 102 and on the display 114 of the PIN entry device 104 as part of the execution of the patient verification routine 200, as will be explained in conjunction with the discussion of the patient verification routine 200 below. In one embodiment, the graphical user interfaces may be provided as the web pages served by the application server 106 which acts as a web server, and the pages are displayed on the display 112 by the web browser applications on the pharmacy workstation 102, providing a graphical user interface by which pharmacists may interact with the patient verification system 100. Likewise, the pages may be displayed on the display 114 by a web browser application on the PIN entry device 104 or by a web browser application on the pharmacy workstation 102, which, in turn, causes the PIN entry device 104 to display the pages, to provide a graphical user interface by which patents may interact with the patient verification system 100. Of course, it will be understood by those of ordinary skill in the relevant art(s) that the workstation 102 and/or the PIN entry device 104 may each have their own user interface applications to display the screenshots of FIGS. 3-10 as part of the patient verification routine 200.

Figure 3:
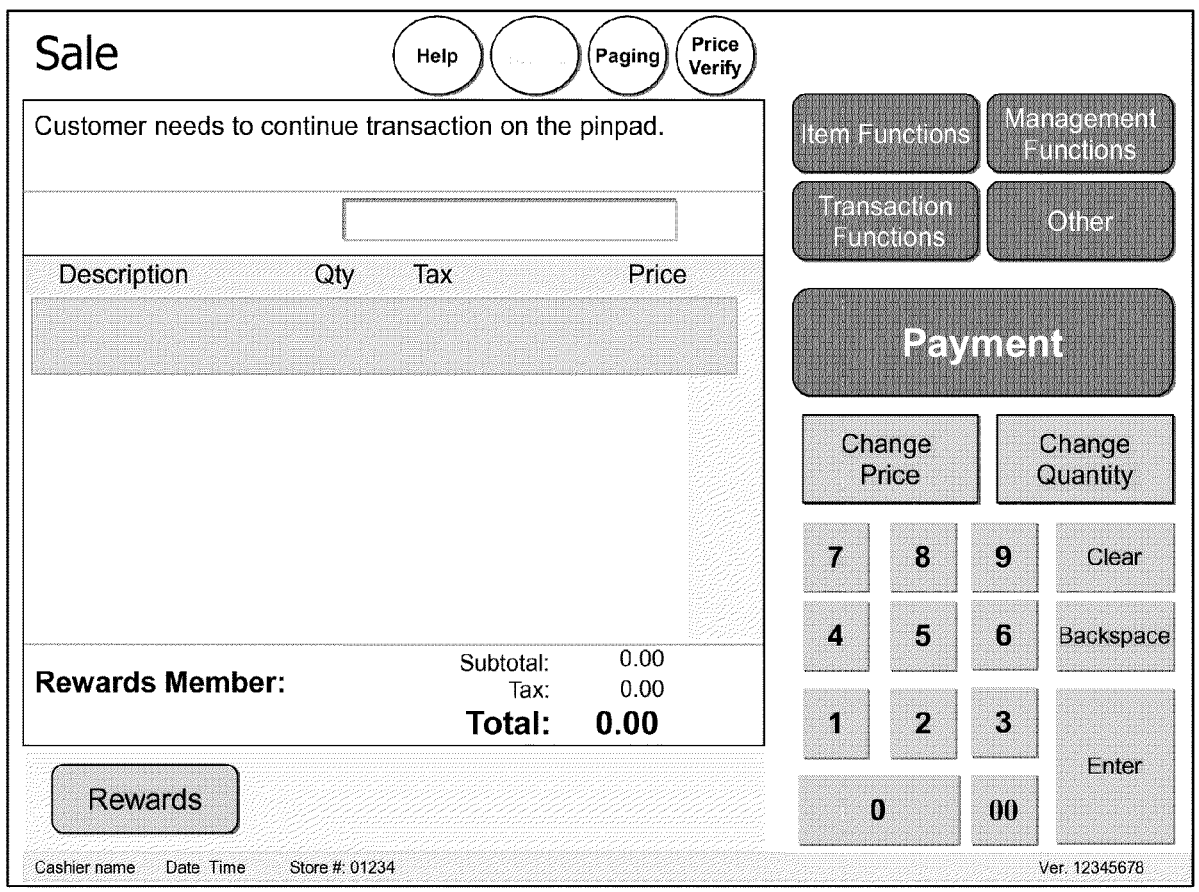
FIG. 3 is a screen shot of a prescription transaction user interface page.

Referring to FIG. 2 and beginning at block 202, during a transaction for a prescription the patient verification routine 200 prompts for input regarding a loyalty program membership. In other words, the patient verification routine 200 prompts as to whether or not the patient is a patient member of the health and wellness rewards program. The prompt may be presented to both the patient and the pharmacist. For example, FIG. 3 is a screen shot of a prescription transaction user interface page that may be displayed on the display 112 of the workstation 102. As shown in FIG. 3, the prescription transaction user interface page prompts the pharmacist with the message "Customer needs to continue transaction on the pinpad," where the "pinpad" refers to the PIN entry device 104. At this juncture, the patient verification routine 200 may temporarily stop the transaction from proceeding until an entry is provided regarding a health and wellness rewards program membership. The display of FIG. 3 notifies the pharmacist of this requirement, which, in turn, the pharmacist may use to prompt the patient to provide an input to the PIN entry device 104. FIG. 3 may also provide the pharmacist with the option of opting out of having the patient provide an entry for a health and wellness rewards program membership, if, for example, the pharmacist is informed that the patient declines to provide the information or does not have a health and wellness rewards membership.

Figure 4:
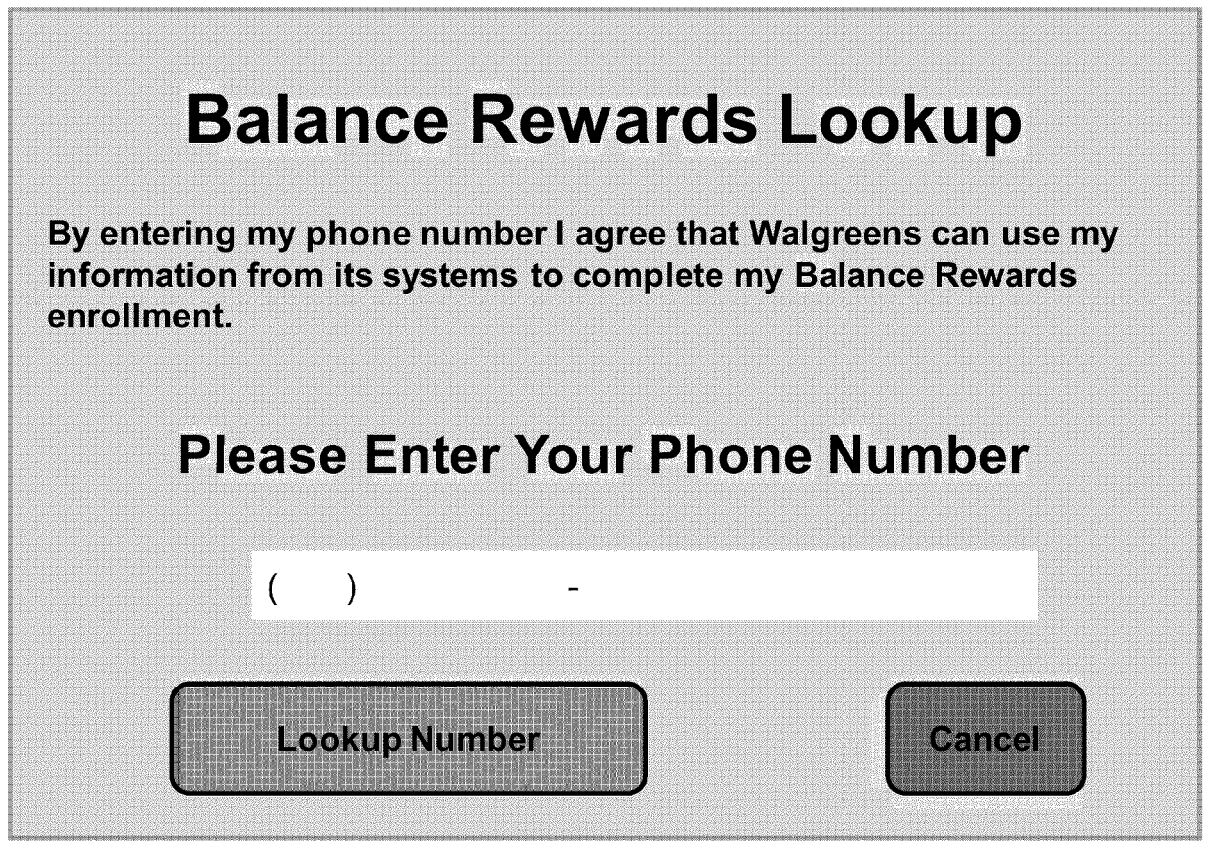
FIG. 4 is a screen shot of a health and wellness rewards program look-up PIN entry device interface page.

FIG. 4 is a screen shot of a health and wellness rewards program membership look-up interface page that may be displayed on the display 114 of the PIN entry device 104. The screen shot of FIG. 4 may be displayed on the display 114 concurrently with the screen shot of FIG. 3 displayed on the display 112. Assuming the patient is a patient member of the health and wellness rewards program, the patient may enter his/her phone number or other identifying information associated with the health profile 126 as prompted by the screen shot in FIG. 4 using the keypad 116. Alternatively, the patient may enter membership identification information associated with the health and wellness rewards program membership, which may be used by the system 100 to retrieve identifying information, such as the patient's phone number, from the patient's health profile 126.

In yet another alternative, the patient may scan a rewards membership indicia, such as a rewards card with a magnetic strip, bar code or RFID tag, using the membership identification reader 118, or interface his/her smartphone with the PIN entry device 114 to read information from the phone. In one embodiment, the information read by the PIN entry device 114 may be the phone number or other identifying information read directly from the rewards membership indicia or smartphone. Alternatively, the information read by the PIN entry device 114 may be an account number, name or other membership identification information, which is used by the workstation 102 and/or application server 106 to look up the health profile 126 associated with the membership identification information and to read the patient's phone number or other identifying information as stored in the health profile 126. FIG. 4 also provide the patient with the option to cancel out of providing a phone number associated with a health and wellness rewards membership or providing a rewards membership identification, if, for example, the patient simply does not want to provide the information or the patient does not have a health and wellness rewards program membership.

Referring back to FIG. 2, the patient verification routine 200 determines whether a health and wellness rewards program membership has been identified at block 204, either by the patient entering a phone number or by otherwise providing identifying information, such as by scanning a health and wellness rewards program card using the reader 118, for example. If a health and wellness rewards program membership has been identified, the patient verification routine 200 reads the phone number associated with the health and wellness rewards program membership at block 206. As stated above, the phone number may be that entered by the patient using the keypad 118, as read from membership identification information (e.g., as read from the scan of the health and wellness rewards program card) or as read from the health profile 126 associated with the health and wellness rewards membership.

At block 208, the patient verification routine 200 reads the phone number or other identifying information associated with the prescription that is the subject of the transaction. In particular, once the phone number for the health and wellness rewards membership is read, the pharmacist may scan the prescription leaflet for the prescription. The prescription leaflet is printed medication information that accompanies the prescription that includes, among other information, the name of the prescription medication, how the medication works, effects of the medication, indications and usage, contraindications, warnings and precautions, potential adverse reactions, dosage and administration. In addition, printed indicia may be provided, such as, for example, a barcode which may be scanned by the pharmacist using a barcode reader. Of course, other indicia, whether printed or embedded (e.g., an RFID tag) with the prescription leaflet may be scanned or otherwise read from the prescription leaflet once the phone number for the health and wellness rewards membership is read.

Scanning the prescription leaflet results in reading the phone number associated with the prescription at block 208, in addition to reading and/or retrieving the patient prescription profile from the data store 120. For example, the indicia provided on or with the prescription leaflet may include the phone number associated with the prescription embedded and/or encrypted in the indicia. Alternatively, the indicia provides identification of a patient prescription profile 122 associated with the patient and the patient's prescription. From the patient prescription profile 122, the patient verification routine 200 may read the phone number associated with the prescription.

Generally speaking, at the time of this application it is important for the phone number or other identifying information for the health and wellness rewards membership to be read prior to reading the phone number or other identifying information associated with the prescription. This is because the United States Health Insurance Portability and Accountability Act of 1996 (HIPAA) prohibits non-health information from being intermingled with private health information. This means that information for a health and wellness rewards program, as may be stored in the health profiles 126, cannot include private health information as may be stored in the patient prescription profiles 122, even if some of the information is the same. As a result, the systems 108 and 110, and particularly the data stores 128, 120, are separately maintained as logically disparate so as to keep the information contained therein logically disparate. Likewise, as a result, information from the patient prescription profile 122 cannot be read into the health profile 126, though information from the health profile 126 can be read into the patient prescription profile 122.

If the prescription leaflet is scanned before input regarding a rewards program membership, reading the health and wellness rewards membership phone number, or reading or retrieving information from the patient prescription profile 122, the patient verification routine 200 may deem this action as non-entry of an input regarding a rewards program membership at block 204, and therefore consider the health and wellness rewards program membership to not exist or to ignore any input regarding a health and wellness rewards program membership even if such membership does exist. This assists in maintaining compliance with HIPAA or other health information privacy regulations.

At block 210, the patient verification routine 200 compares the health and wellness rewards membership phone number read at block 206 with the prescription phone number read at block 208. Again, to maintain compliance with HIPAA or other privacy regulations, the health and wellness rewards membership phone number is matched with (compared against) the prescription phone number, not vice versa. Further, as previously disclosed, identifying information other than a phone number may be used in the disclosed process and system, though the identifying information compared at block 210 should be of the same type (e.g., an address read at block 206 with an address read at block 208, a passcode read at block 206 with a passcode read at block 208, etc.).

Figure 5:
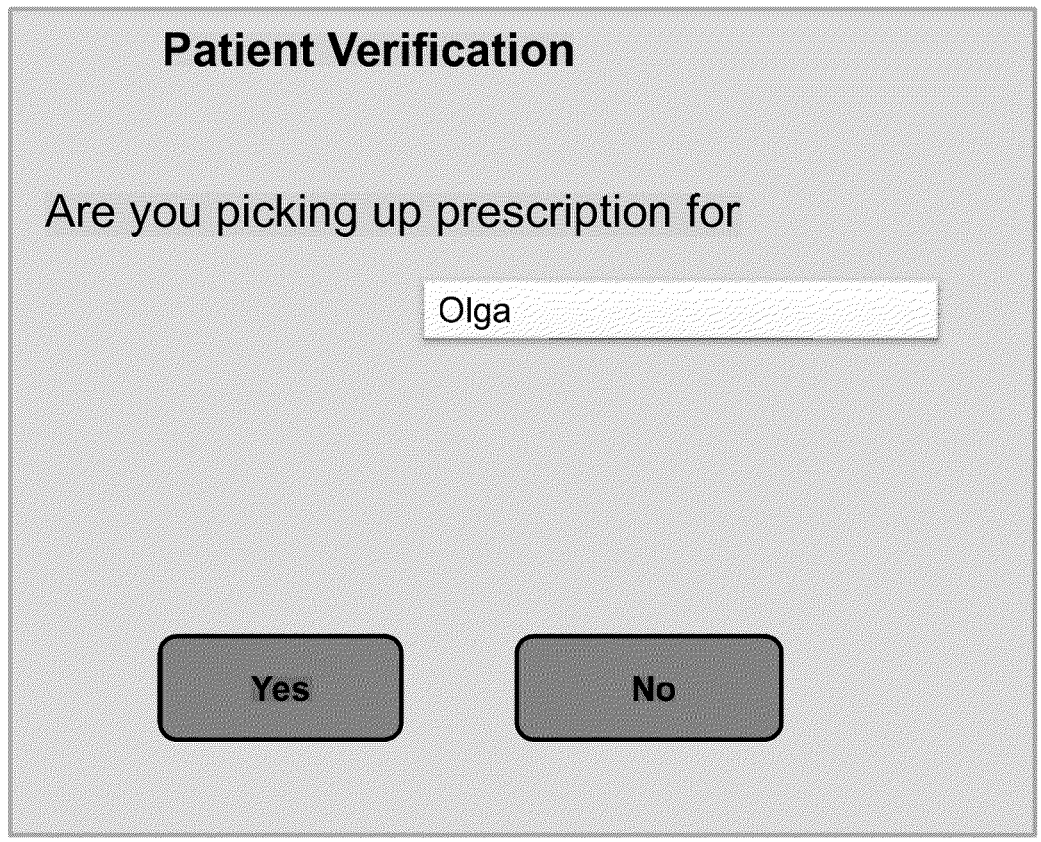
FIG. 5 is a screen shot of a patient identity verification PIN entry device interface page.

If there is a match between the phone numbers as determined at block 210, the patient verification routine 200 prompts the patient to verify that he/she is there for pick up a prescription for him/herself at block 212. The patient verification routine 200 may therefore cause the display 116 to present the page as shown in FIG. 5, where FIG. 5 is a screen shot of a patient identity verification PIN entry device interface page. The name verification prompt may simply be the first name associated with the prescription. In another embodiment, the patient verification routine 200 may read the patient's name from both the health and wellness rewards information and the patient prescription information. Provided the names match, the patient verification routine 200 may forego block 212 and automatically proceed to add the prescription to the transaction at block 216. If the names do not match, the patient verification routine 200 may prompt the patient at block 212 as described above and present the name associated with the prescription information.

As mentioned above, the person picking up the prescription may not, in fact, be the patient, but rather be a person authorized to pick up the prescription on behalf of the actual patient, such as, for example, a parent picking up a prescription for a child or a person picking up a prescription on behalf of his/her spouse. As such, the prompt at block 212 and the interface page of FIG. 5 may display the name of the actual patient rather than the person picking up the prescription, in which case the prompt may be presented to verify that the person is there to pick up for the actual patient, provided that the patient and the person picking up the prescription share the same phone number.

Figure 6:
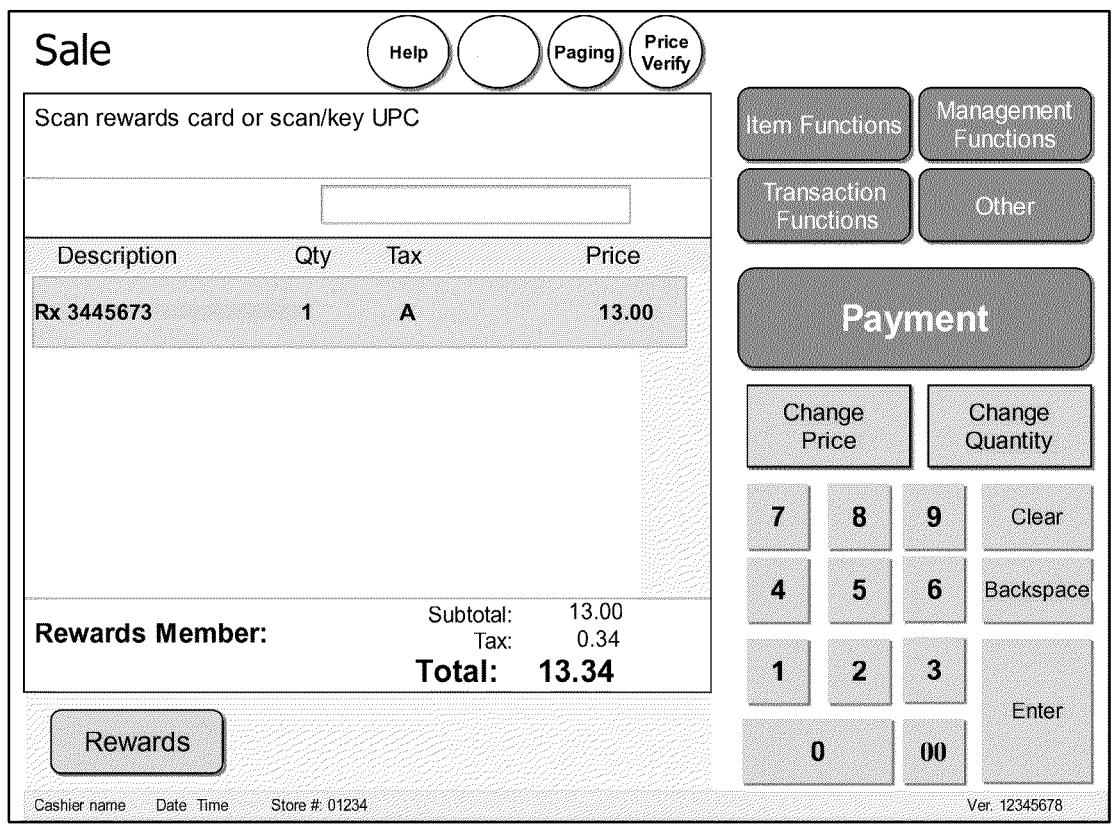
FIG. 6 is a screen shot of a prescription transaction user interface page adding a verified prescription to the transaction.
Figure 7:
FIG. 7 is a screen shot of a prescription transaction PIN entry device interface page to complete the transaction.

If the patient confirms that he/she is picking up the prescription for the name presented on the display 116, as determined at block 214, the prescription may be added to the transaction at block 216. Adding the prescription to the transaction at block 216 causes the display 112 to present the page as shown in FIG. 6, where FIG. 6 is a screen shot of a prescription transaction user interface page adding a verified prescription to the transaction. At this juncture, the patient verification routine 200 may also cause the display 114 to present the page as show in FIG. 7, where FIG. 7 is a screen shot of a prescription transaction PIN entry device interface page to complete the transaction.

If there are multiple prescriptions to be made part of the transaction, the prescription leaflets may likewise be scanned as described above. If there are multiple prescriptions associated with the same phone number and patient as read from scanning the leaflets, those prescriptions may be automatically added to the transaction without additional verification. On the other hand, if there are multiple prescriptions associated with the same phone number but for different patients, such as a first prescription for the patient picking up the prescription and a second prescription for a family member of the same household (and hence, same phone number), the patient verification routine 200 may revert back to block 212 and prompt the patient to verify the name of the person for whom the prescription is being picked up, and proceed through the remainder of the patient verification routine 200 as described above.

Figure 8:
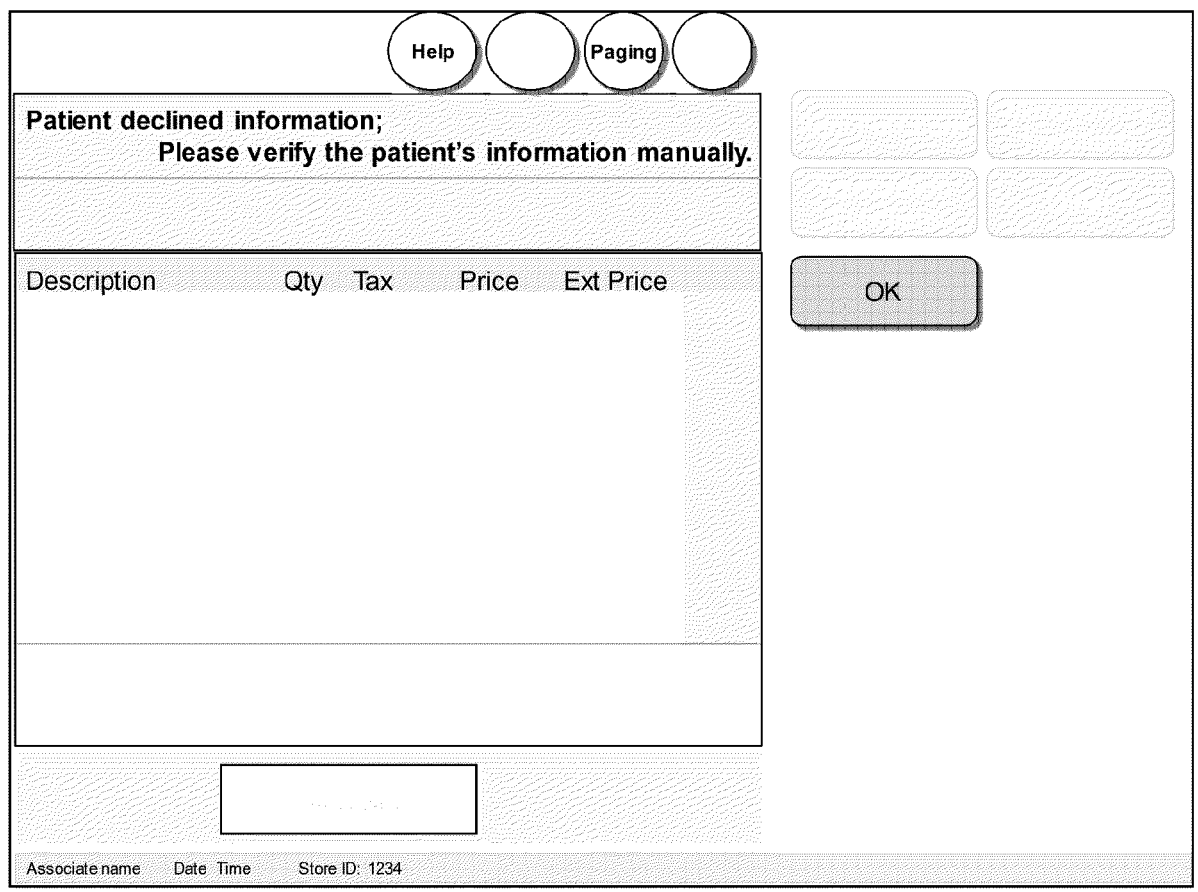
FIG. 8 is a screen shot of a prescription transaction user interface page declining patient identity verification.
Figure 9:
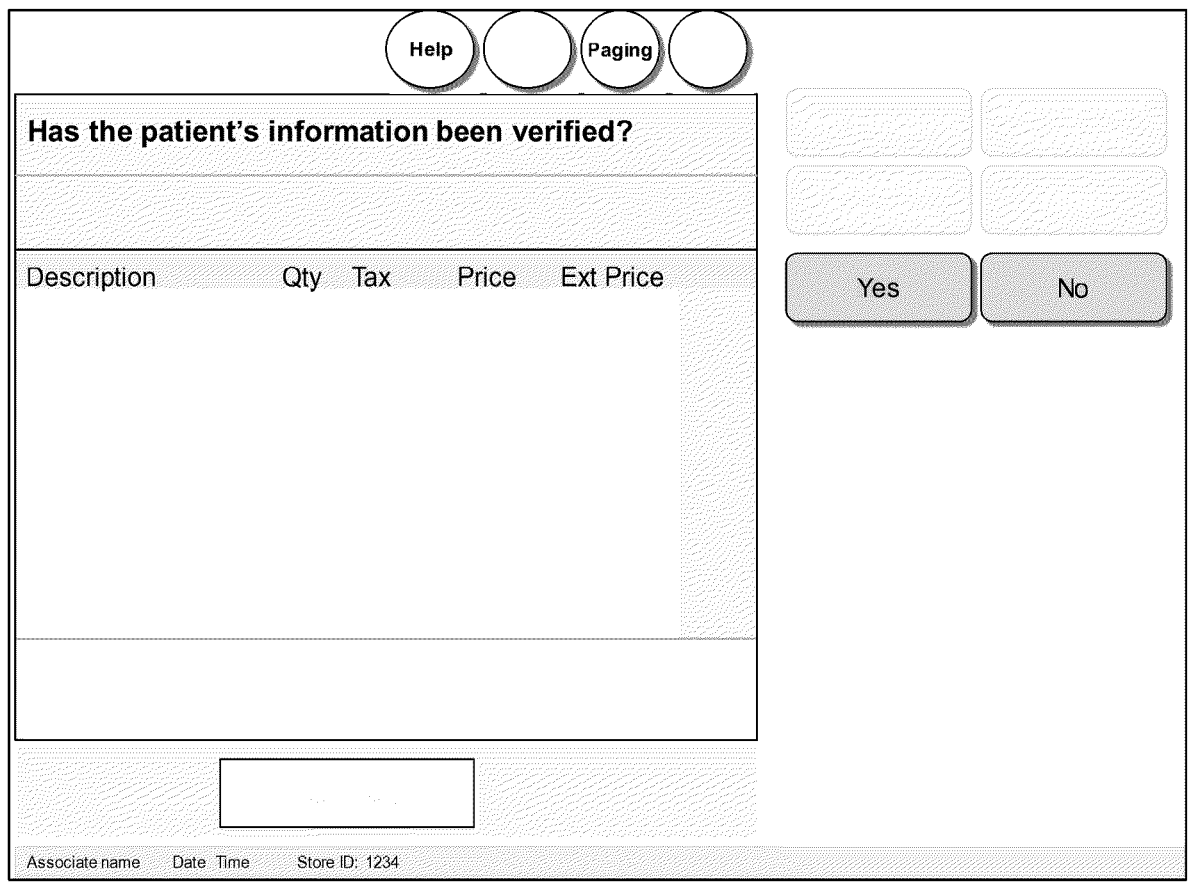
FIG. 9 is a screen shot of a prescription transaction user interface page for manual patient identity verification.

Referring back to block 214 of the patient verification routine 200, if the patient does not verify that he/she is picking up the prescription for the name displayed in the page as shown in FIG. 5, for example if the patient selects "No", the patient verification routine 200 may prompt the pharmacist to manually complete the verification at block 224. As part of this prompt, the patient verification routine 200 may cause the display 112 to present the page as shown in FIG. 8, where FIG. 8 is a screen shot of a prescription transaction user interface page declining patient identity verification. As shown therein, the interface page may prompt the pharmacist with the message "Patient declined information; Please verify the patient's information manually." The pharmacist may thereafter select "OK" and ask the patient to confirm another piece of identifying information associated with the prescription, such as the patient's address or the like. Provided the information provided by the patient matches with that in the patient prescription profile 122, the pharmacist may override the patient verification routine 200 and add the prescription to the transaction. For example, the patient verification routine 200 may cause the display 112 to present the page as shown in FIG. 9, where FIG. 9 is a screen shot of a prescription transaction user interface page for manual patient identity verification. If the information provided by the patient in response to the pharmacist's inquiry matches that provided in the patient prescription profile 122, the pharmacist may select "Yes" and the prescription will be added to the transaction. If not, the pharmacist may select "No" and the transaction will be blocked.

Referring back to block 210, if the patient verification routine 200 determines that the health and wellness rewards membership phone number read at block 206 with the prescription phone number read at block 208 do not match, the patient verification routine 200 may prompt the patient to enter the phone number associated with the prescription as stored in the patient prescription profile 122. The patient verification routine 200 may thereby cause the display 114 to present the page shown in FIG. 10, where FIG. 10 is a screen shot of a patient profile look-up PIN entry device interface page. In the example shown, the patient verification routine 200 prompts the patient for only the last four digits of the prescription phone number, though the patient may be prompted for any other part or all of the prescription phone number. If the phone number entered by the patient at block 220 matches the prescription phone number associated with the prescription as determined at block 222, the patient verification routine 200 proceeds to block 212 to prompt the patient for verification that he/she is there for pick up a prescription for him/herself, and the patient verification routine 200 may proceed at block 212 as set forth above. If the phone numbers do not match as determined at block 222, the patient verification routine 200 may proceed with a manual verification as discussed with referent to block 224. Alternatively, the patient verification routine 200 may prompt the patient again in the event of a mismatch, though after multiple mismatches the patient verification routine 200 may thereafter proceed to block 224. The patient may also simply not know the phone number associated with the prescription, and select "Don't know."

Referring back to block 204, if a health and wellness rewards program membership has not been identified, the patient verification routine 200 may proceed to read the prescription phone number at block 218 without reading a phone number associated with a health and wellness rewards program membership. The prescription phone number may be read at block 218 in the same or similar manner as reading the prescription phone number at block 208. For example, the patient may decline to enter a phone number when presented with the interface page shown in FIG. 4 by selecting "Cancel", at which point the pharmacist proceeds to scan the prescription leaflet and the patient verification routine 200 read the prescription phone number at block 218. In another example mentioned above, the prescription leaflet may be scanned before entry of a phone number associated with the health and wellness rewards program membership, in which case the patient verification routine 200 will automatically revert to reading the prescription phone number at block 218.

By implementing a patient verification system as described herein, a pharmacy may better serve its patients by providing services that will help verify the patient is receiving the correct prescription. Such services may be provided in a setting that will improve the pharmacy's relations with its customers and improve overall quality of care by reducing or eliminating variations, inconsistency or human bias.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in exemplary configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present system and methods have been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention. This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A computer-implemented method for increasing patient safety corresponding to fulfillments of prescriptions for pharmaceutical products, the method comprising, at a system including a first device and a second device:

receiving, at the first device, an input of a first indicia indicating a member of a rewards program;

based on the first indicia indicating the member of the rewards program, identifying and retrieving, via a wide area network coupling the first device and the second device to a backend system from a rewards database that is included in the backend system and that stores a plurality of profiles of a plurality of members of the rewards program, a profile associated with the member of the rewards program, the profile containing first data identifying the member of the rewards program;

subsequent to receiving the input of the first indicia, receiving, at the second device, an input of a second indicia indicating a patient for whom a prescription for a pharmaceutical product was prescribed, the second indicia being different than the first indicia;

based on the second indicia indicating the patient, identifying and retrieving, via the wide area network from a patient database that is included in the backend system and separately maintained as logically disparate from the rewards database, and that stores a plurality of prescription profiles associated with a plurality of patients, a prescription profile associated with the patient associated with the prescription, the prescription profile containing second data identifying the patient, and wherein the second data from the patient database does not intermingle with the first data from the rewards database;

when the first data and the second data match, thereby verifying an identity of the patient, displaying, at the second device, an indication to proceed with a transaction for the pharmaceutical product; and when the first data and the second data do not match, temporarily stopping the transaction for the pharmaceutical product and displaying, at the second device, a prompt for a manual verification of the identity of the patient.

2. The computer-implemented method of claim 1, wherein the first device is adapted to prompt for entry of verification that a name displayed on the first device is the name of a recipient of the prescription when the first data and the second data match.

3. The computer-implemented method of claim 2, wherein first device and the second device are adapted to proceed with the transaction for the pharmaceutical product in response to a verifying input verifying the name displayed on the first device is the name of the recipient of the prescription.

4. The computer-implemented method of claim 2, wherein first device and the second device are adapted to deny the transaction for the pharmaceutical product in response to a denying input indicating the name displayed on the first device is not the name of the recipient of the prescription.

5. The computer-implemented method of claim 1, wherein the rewards database and the patient database are separately maintained in accordance with government regulations.

6. The computer-implemented method of claim 1, wherein the rewards program is a structured marketing effort that rewards certain behavior by the member.

7. The computer-implemented method of claim 1, wherein the first indicia indicating the member of the rewards program is encoded.

8. The computer-implemented method of claim 7, wherein the first device is adapted to decode the first indicia.

9. A system for increasing patient safety corresponding to fulfillments of prescriptions for pharmaceutical products, the system comprising:
a first device;
a second device;
a rewards database storing rewards data of a plurality of members of a reward program, the rewards database included in a backend system coupled to the first device and to the second device via a wide area network;

a patient database storing patient data of a plurality of patients, the patient database included in the backend system and separately maintained as logically disparate from the rewards database, and the patient data from the patient database does not intermingle with the rewards data from the rewards database; and a non-transitory program memory communicatively coupled to the first device and the second device and storing executable instructions that, when executed, cause the system to:

receive, at the first device, an input of a first indicia indicating a member of a rewards program;

based on the first indicia indicating the member of the rewards program, identify and retrieve, via the wide area network from the rewards database, a profile associated with the member of the rewards program, the profile containing first data identifying the member of the rewards program;

subsequent to receiving the input of the first indicia, receive, at the second device, an input of a second indicia indicating a patient for whom a prescription for a pharmaceutical product was prescribed, the second indicia being different than the first indicia;

based on the second indicia indicating the patient, identify and retrieve, via the wide area network from the patient database, a prescription profile associated with the patient associated with the prescription, the prescription profile containing second data identifying the patient;

when the first data and the second data match, thereby verifying an identity of the patient, display, at the second device, an indication to proceed with a transaction for the pharmaceutical product; and when the first data and the second data do not match, temporarily stop the transaction for the pharmaceutical product and display, at the second device, a prompt for a manual verification of an identity of the patient.

10. The system of claim 9, wherein the first indicia indicating the member of the rewards program is encoded.

11. The system of claim 10, wherein the first device is adapted to decode the first indicia.

12. The system of claim 9, wherein the first device is a point-of-sale retail personal identification number entry device.

13. The system of claim 12, wherein the second device is a workstation operatively coupled to the point-of-sale retail personal identification number entry device.

14. The system of claim 9, wherein the first device is adapted to prompt for entry of verification that a name displayed on the first device is the name of a recipient of the prescription when the first data and the second data match.

15. The system of claim 14, wherein first device and the second device are adapted to proceed with the transaction for the pharmaceutical product in response to a verifying input verifying the name displayed on the first device is the name of the recipient of the prescription.

16. The system of claim 14, wherein first device and the second device are adapted to deny the transaction for the pharmaceutical product in response to a denying input indicating the name displayed on the first device is not the name of the recipient of the prescription.

17. The system of claim 9, wherein the rewards database and the patient database are separately maintained in accordance with government regulations.

18. The system of claim 9, wherein the rewards program is a structured marketing effort that rewards certain behavior by the member.

19. A tangible, non-transitory computer-readable medium storing executable instructions for increasing patient safety corresponding to fulfillments of prescriptions for pharmaceutical products, the instructions, when executed by at least one processor of a computer system, causing the computer system to:
- receive, at a first device, an input of a first indicia indicating a member of a rewards program;
- based on the first indicia indicating the member of the rewards program, identify and retrieve, via a wide area network coupling the first device and the second device to a backend system from a rewards database that is included in the backend system and that stores a plurality of profiles of a plurality of members of the rewards program, a profile associated with the member of the rewards program, the profile containing first data identifying the member of the rewards program;
- subsequent to receiving the input of the first indicia, receive, at a second device, an input of a second indicia indicating a patient for whom a prescription for a pharmaceutical product was prescribed, the second indicia being different than the first indicia;
- based on the second indicia indicating the patient, identify and retrieve, via the wide area network from a patient database that is included in the backend system and separately maintained as logically disparate from the rewards database, and that stores a plurality of prescription profiles associated with a plurality of patients, a prescription profile associated with the patient associated with the prescription, the prescription profile containing second data identifying the patient;
- when the first data and the second data match, thereby verifying an identity of the patient, display, at the second device, an indication to proceed with a transaction for the pharmaceutical product; and
- when the first data and the second data do not match, temporarily stop the transaction for the pharmaceutical product and display, at the second device, a prompt for a manual verification of the identity of the patient.

20. The non-transitory computer-readable medium of claim 19, the instructions further causing the system to:
- prompt, on the first device, for entry of verification that a name displayed on the first device is the name of a recipient of the prescription when the first data and the second data match.

* * * * *